United States Patent [19]

Rivier et al.

[11] 4,216,141

[45] Aug. 5, 1980

[54] METHOD FOR CYCLIZATION OF PEPTIDES

[75] Inventors: Jean E. F. Rivier, La Jolla; Robert F. Galyean, San Marcos, both of Calif.

[73] Assignee: The Salk Institute for Biological Studies, San Diego, Calif.

[21] Appl. No.: 926,491

[22] Filed: Jul. 19, 1978

Related U.S. Application Data

[63] Continuation of Ser. No. 798,441, May 23, 1977, abandoned.

[51] Int. Cl.$^2$ .................. C07C 103/52; C07C 149/00
[52] U.S. Cl. ...................... 260/112.5 R; 260/112.5 T; 260/112.5 S
[58] Field of Search ................. 260/112.5 R, 112.5 T, 260/112.5 S

[56] References Cited

U.S. PATENT DOCUMENTS

| | | | |
|---|---|---|---|
| 3,318,864 | 5/1967 | Boissonas et al. | 260/112.5 R |
| 3,497,491 | 2/1970 | Zaoral et al. | 260/112.5 R |
| 3,749,705 | 7/1973 | Sakakibara et al. | 260/112.5 R |
| 3,883,498 | 5/1975 | Gillessen et al. | 260/112.5 R |
| 3,994,871 | 11/1976 | Kamber et al. | 260/112.5 R |
| 4,033,940 | 7/1977 | Hughes et al. | 260/112.5 R |

OTHER PUBLICATIONS

L. Zervas, et al., J. A. C. S. 87, 1965, pp. 4922–4933.
Hope, et al., J. Biol. Chem. 237, 1962, pp. 1563–1566.

*Primary Examiner*—Delbert R. Phillips
*Attorney, Agent, or Firm*—Fitch, Even & Tabin

[57] ABSTRACT

Peptides containing a disulfide bond between two cysteine residues are formed by an oxidation process. The oxidation step is accomplished under conditions whereby the sulfhydryl concentration in a reaction mixture is maintained at substantially zero during the reaction. In the process, an aqueous solution of a peptide containing at least one pair of cysteine moieties is added incrementally to a buffered solution containing an oxidizing agent. The period between addition of the increments of the peptide solution is sufficient that the reaction to form the disulfide bond occurs substantially instantaneously. The increments are of such size that the sulfhydryl concentration during the reaction remains substantially constant and at a level of substantially zero, equivalent to infinite dilution.

12 Claims, No Drawings

METHOD FOR CYCLIZATION OF PEPTIDES

The invention described herein was made in the course of work under a grant or award from the Department of Health, Education, and Welfare.

This is a continuation of application Ser. No. 798,441, filed May 23, 1977, now abandoned.

The present invention relates generally to cyclization of peptides. More particularly, the present invention relates to methods for treating peptides containing an even number of cysteine groups to produce a disulfide bond between pairs of such groups and to form a ring structure. The method of the invention is useful in the synthesis of peptides which have biological activity and which have therapeutic value in the treatment of certain diseases in animals and man.

Many peptides which contain a disulfide ring are known which are biologically active and are useful in the treatment of diseases. Somatostatin, which is described in U.S. Pat. No. 3,904,594 to Guillemin et al, has been shown to be effective in the inhibition of growth hormone by the pituitary gland. Somatostatin has been proposed for use in the treatment of acromegaly and diabetes. Somatostatin contains a disulfide bond between the cysteine residues in positions 3 and 14 in its amino acid sequence. Vasopressin and its analog lypressin are used as antidiuretic drugs in man. These peptides contain a disulfide bridge structure between cysteine groups at positions 1 and 6 in their amino acid sequences. Oxytocin is used for the induction or stimulation of labor in humans in animals and also to control postpartum uterine bleeding. Oxytocin contains a disulfide bridge structure between the cysteine groups at positions 1 and 6 in its amino acid chain. Calcitonins contain a ring structure involving cysteine groups at the first and seventh positions in their amino acid chain. Calcitonins are useful in the treatment of Paget's disease.

The amino acid sequence of the above described biologically active peptides containing cysteine groups joined by a disulfide bond in a ring structure are set forth in Table 1, hereinbelow:

It is known to prepare synthetically a peptide having a closed disulfide ring structure by forming the non-cyclic peptide having the desired amino acid sequence and then subjecting the peptide to an oxidative process using oxidizing agents to form the disulfide bond between two cysteine residues. The most frequently used oxidative process for producing peptides having a disulfide bond between two cysteine residues is described in the literature Hope E. D., Murti B. X. and duVigneaud V., J. Biol. Chem., V.237, page 1563 (1962). This method is commonly referred to as the duVigneaud Method. In the duVigneaud Method, a buffered solution of the linear peptide containing at least a pair of cysteine groups is oxidized by adding a buffered solution of a ferricyanide salt to the peptide solution at a constant pH.

A main disadvantage of the duVigneaud Method and other oxidative processes is the exposure of the highly reactive peptide molecule to oxidizing agents and to the formation of cross linking and polymerization of the peptide molecules. The known oxidative methods for forming a closed disulfide ring structure can cause inactivation of the peptide and a lower yield of biologically active peptide product.

A recent patent, U.S. Pat. No. 3,929,758 to Hughes et al, describes a further method for the synthesis of disulfide cyclic peptide. In the method of the Hughes patent a disulfide cyclic peptide is prepared by first preparing a peptide containing at least two cysteine moieties one of which is protected by an n-alkylthio group. Thereafter the protected peptide is subjected to a procedure in which the peptide is held in solution substantially free of oxygen at a pH of 5 to 10 until rearrangement takes place to yield a cyclic disulfide peptide. During the rearrangement the n-alkylthio group is displaced from the amino acid chain. This method is not wholly satisfactory in that it involves a separate step of preparing the n-alkylthio protected cysteine peptide. The method is also more time consuming than the simple oxidative methods which have been heretofore used.

It would be desirable to provide a method for the formation of a disulfide bond between pairs of cysteine moieties of a peptide by an oxidative process which does not result in inactivation of the peptide cross linking of peptide molecules or polymerization.

Accordingly, a principal object of the present invention is the provision of a method for cyclization of a peptide containing at least two cysteine moeities by an oxidative process.

It is another object to provide an oxidative method for the cyclization of peptides containing cysteine moieties which minimizes the formation of cross linking and polymerization of peptide molecules.

Generally, in accordance with various features of the present invention, peptides containing a disulfide bond between two cysteine residues are formed by a procedure that does not require the formation of intermediates prior to forming the disulfide bond. The process involves a simple oxidation of a peptide containing at least two cysteine moieties. The oxidation step is accomplished under conditions whereby the sulfhydryl

TABLE 1

TYPICAL PEPTIDES CONTAINING CYSTEINE RING STRUCTURES

Somatostatin:
H—ALA—GLY—CYS—LYS—ASN—PHE—PHE—TRP—LYS—THR—PHE—THR—SER—CYS—OH
(disulfide bond between the two CYS residues)

Vasopressin:
H—CYS—TYR—PHE—GLN—ASN—CYS—PRO—ARG—GLY—NH$_2$
(disulfide bond between the two CYS residues)

Oxytocin:
H—CYS—TYR—ILE—GLN—ASN—CYS—PRO—LEU—GLY—NH$_2$
(disulfide bond between the two CYS residues)

Human Calcitonin:
H—CYS—GLY—ASN—LEU—SER—THR—CYS—MET—LEU—GLY—THR—TYR—THR—GLN—ASP—PHE—
ASN—LYS—PHE—HIS—THR—PHE—PRO—GLN—THR—ALA—ILE—GLY—VAL—GLY—ALA—PRO—NH$_2$
(disulfide bond between the two CYS residues)

concentration in a reaction mixture is maintained at substantially zero during the reaction. The process involves the formation of an acidified aqueous solution of a peptide containing at least one pair of cysteine moieties. Thereafter, the acidic peptide solution is added incrementally to a buffered solution containing an oxidizing agent. The period between addition of the increments of acidic peptide solution is such that the oxidizing reaction to form the disulfide bond occurs substantially instantaneously and the increments are of such size that the sulfhydryl concentration during the reaction remains substantially constant and at a level of substantially zero equivalent to infinite dilution.

The sulfhydryl groups of the cysteine moieties can be protected prior to addition of the peptide solution to the oxidizin solution provided that a suitable deprotection agent is present in the oxidizing solution. In this embodiment the sulfhydryl groups are generated in situ. One suitable means of protecting the sulfhydryl groups is to form salts thereof with a suitable cation and to provide a suitable anion in the oxidizing solution which forms an insoluble salt with the cation. Suitable cations are silver and mercury. A suitable anion for silver is chloride and a suitable anion for mercury is sulfide.

The process of the invention is applicable to the synthesis of any cyclic disulfide peptide where the disulfide bond is between at least one pair of cysteine residues in the amino acid chain. The process is particularly suitable for the synthesis of labile, biologically active peptides because the disulfide bond is formed under conditions which avoid cross linking and polymerization of the peptide and do not otherwise disturb peptide structure.

The process of the invention starts with the preparation of the peptide by building the amino acid chain sequence of any peptide containing at least two cysteine residues. The amino acid chain sequence may be assembled by use of classical synthesis techniques or by solid phase techniques. The solid phase technique method for the preparation of peptides is generally described in Merrifield R. B., Advances in Enzymology, Inter Science, New York, N.Y. 1969, Chapter 32, 221-296, and Stewart J. & Young J. Solid Phase Peptide Synthesis, W. H. Freeman & Co., San Francisco 1969. The synthesis of somatostatin is described in detail in U.S. Pat. No. 3,904,594 to Guillemin et al.

Solid phase synthesis is usually preferred because of the flexibility for preparation of any desired peptide. In this synthesis method the first amino acid is attached to a resin and the remaining amino acids are added one at a time until the total peptide sequence has been built up on the resin. The functional groups of the amino acids are protected by blocking groups during the formation of the peptides. The $\alpha$-amino group of the amino acids is usually protected by a tertiary butyloxycarbonyl group (Boc) or an equivalent thereof.

The hydroxyl functions of serine and threonine are usually protected by a benzyl or benzyl derivative group (BZ) such as 4-methoxybenzyl, 4-methylbenzyl, 3,4-dimethylbenzyl, 4-chlorobenzyl, 2,6-dichlorobenzyl, 4-nitrobenzyl, benzhydryl, or an equivalent thereof. The hydroxyl function of tyrosine may be unprotected, may be protected by a benzyl or benzyl derivative group as described above, or may be protected by a benzyloxycarbonyl or a benzyloxycarbonyl derivative such as 2-chlorobenzyloxycarbonyl or a 2-bromobenzyloxycarbonyl group or equivalent thereof. The guanidino function of arginine may be protected by a nitro group, a tosyl group or an equivalent thereof. The $\alpha$-amino function of lysine may be protected by a benzyloxycarbonyl group or a benzylozycarbonyl derivative such as 2-chlorobenzyloxycarbonyl, 2-bromobenzyloxycarbonyl, 3,4-dimethylbenzyloxycarbonyl or the equivalent thereof. The protective groups used on the imidazole nitrogen of histine may be Tosyl group and dinitro phenyl group or the equivalent thereof.

The peptides to which the improved cyclizing process of the invention is applicable have at least two cysteine groups and these groups may be protected by a benzyl or benzyl derivative group which is removed in the subsequent acid treatment along with other protective groups which may then remain.

The amino acid in the highest numbered position in the chain of the peptide to be synthesized is coupled to the resin using the protective groups as above described followed by removal of the BOC protective groups for the $\alpha$-amino group. The next amino acid is coupled to the amino acid last added using appropriate protective groups as above set forth and the BOC protective group removed etc. until the desired chain of amino acids is completed. Suitable combinations of two or more amino acid groups with appropriate protective groups may be obtained and these combintions reacted with the peptide previously formed to add the combination of amino acid groups. Such combinations may be obtained commercially from chemical supply houses. Finished peptides are also available in protected and deprotected form. The protected form is available either coupled to or cleaved from the resin.

A specific example of the synthesis of somatostatin is given in the following Example 1.

EXAMPLE 1

The synthesis was conducted in a stepwise manner on chloromethylated resin. The resin was composed of fine beads (20-70 microns in diameter) of a synthetic resin prepared by copolymerization of styrene with 1 to 2 percent divinylbenzene. The benzene rings in the resin were chloromethylate in a Friedel-Crafts reaction with chloromethyl methyl ether and stannic chloride. The chlorine thus introduced is a reactive benzyl chloride type of linkage. The Friedel-Crafts reaction is continued until the resin contains 0.5 to 2 millimoles of chlorine per gram of resin. Hereinbelow, in the further description of the synthesis of somatostatin peptides, the reagents used will be first listed by their chemical name and their common abbreviation in parenthesis. Thereafter, the reagent will be referred to by the common abbreviation.

The triethyl ammonium salt cesium or potassium salts of protected Cys was esterified onto the chloromethylated resin by refluxing in ethanol for about 48 hours. The amino group of Cys was protected with t-butyloxycarbonyl (Boc). The S-side chain of Cys was protected with p-methoxybenzyl (MeOBzl). Benzyl (Bzl) can also be used as an S-protecting group.

After deprotection and neutralization, the $N^\alpha$-Boc derivative of the next amino acid, Ser, was added along with a coupling agent, which was dicylohexylcarbodiimide (DCC). The side chain of Ser was protected with benzyl ether (OBzl). Deprotection, neutralization and addition of successive amino acids was performed in accordance with the following schedule:

Schedule for coupling of amino acids other than Asn in solid phase synthesis of Somatostatin

| Step | Reagents and operations | Mix times min. |
|---|---|---|
| 1 | $CH_2Cl_2$ wash 80 ml (2 times) | 3 |
| 2 | Methanol (MeOH) wash 30 ml (2 times) | 3 |
| 3 | $CH_2Cl_2$ wash 80 ml (3 times) | 3 |
| 4 | 50 percent trifluoroacetic acid (TFA) plus 5 percent 1.2 ethanedithiol in $CH_2Cl_2$ 70 ml (2 times) | 10 |
| 5 | $CH_2Cl_2$ wash 80 ml (2 times) | 3 |
| 6 | Triethylamine ($Et_3N$) 12.5% in dimethylformamide (DMF) 70 ml (2 times) | 5 |
| 7 | MeOH wash 40 ml (2 times) | 2 |
| 8 | $CH_2Cl_2$ wash 80 ml (3 times) | 3 |
| 9 | Boc-amino acid (10 mmoles) in 30 ml DMF (1 time) plus dicyclohexylcarbodiimide (DCC) (10 mmoles) in DMF | 30 |
| 10 | MeOH wash 40 ml (2 times) | 3 |
| 11 | $Et_3N$ 12.5% in DMF 70 ml (1 time) | 3 |
| 12 | MeOH wash 30 ml (2 times) | 3 |
| 13 | $CH_2Cl_2$ wash 80 ml (2 times) | 3 |

After step 13, an aliquot is taken for a ninhydrin test: if the test is negative, go back to step 1 for coupling of the next amino acid; if the test is positive or slightly positive, go back to steps 9 through 13.

The above schedule was used for coupling of each of the amino acids of the somatostatin peptide to Cys with the exception of Asn. For Asn steps 1 through 8 are the same and the following schedule is used for the remainder of the coupling reaction:

Schedule for Boc—Asn—ONp coupling in solid phase synthesis of Somatostatin

| Step | Reagents and operations | Mix times min. |
|---|---|---|
| 9 | DMF wash 60 ml (3 times) | 3 |
| 10 | Boc—Asn—ONp (15 mmoles) in 20 ml DMF (1 time) | 800 |
| 11 | MeOH wash 30 ml (4 times) | 3 |
| 12 | $Et_3N$ 12.5 percent in DMF 30 ml (2 times) | 3 |
| 13 | MeOH wash 30 ml (2 times) | 3 |
| 14 | $CH_2Cl_2$ wash 80 ml (3 times) | 31 |

After step 14, an aliquot is taken for a ninhydrin test: if the test is negative go back to step 1 for coupling of the next amino acid: if the test is positive or slightly positive, go back to steps 9 through 14.

$N^\alpha$-Boc protection was used for each of the remaining amino acids throughout the synthesis. OBzl was used as a side chain protecting group for Ser and Thr. P-nitrophenyl (PNp) ester was used to activate the carboxyl end of Asn. O-nitrophenyl ester can also be used for this purpose. Benzyloxycarbonyl (Z) or benzyloxycarbonyl-2Cl [Z (2-Cl)] was used as the protecting group for the Lys side chain. The $N^{-\alpha}$ protecting group for the last amino acid applied to the peptide can be any oxycarbonyl, such as Boc or Z. When the R group of the peptide is an organic acid, the organic acid is attached to the peptide before the peptide is cleaved from the resin. The organic acid is attached to the peptide on the resin by introducing the organic acid in the presence of DCC. The organic acid can also be added by using the organic acid as an N protecting group for the last amino acid added.

Cleavage of the peptides from the resin and deprotection of the side chain protecting groups of the peptide was performed in hydrofluoric acid in the presence of 100 fold molar excess of anisole. After elimination of hydrofluoric acid under high vacuum, the peptide was washed with ether and extracted with degassed dilute acetic acid.

After a peptide has been cleaved from the resin, the peptide is deprotected at least to the extent of forming free sulfhydryl groups on the cysteine moieties to provide a linear form of the peptide. The linear form of the peptide is then dissolved in distilled water which has been acidified to a pH of less than about 5, preferably less than about 4. The peptide is added to the acidified water at level of from about 0.5 to about 10 grams of the peptide per liter of water.

A solution of an oxidizing agent is then prepared. Any suitable oxidizing agent can be used. Suitable oxidizing agents include dibenzoyl peroxide, peracids and ferricyanide salts. A preferred oxidizing agent is any of the soluble ferricyanide salts. Particularly preferred are potassium ferricyanide and sodium ferricyanide. The oxidizing agent is present in the water at a level sufficient to effect oxidation and bridging of each pair of cysteine moieties contained in the peptide solution to be added to the oxidizing solution. In the case of ferricyanide salts, the ferricyanide salt is added to the water at a level of from about 0.5 to about 5 grams of the ferricyanide salt per liter of water. Each liter of the ferricyanide salt solution is sufficient to react with from about 100 ml to about 1 liter of the peptide solution containing from about 1 to about 10 grams of peptide. The solution of the oxidizing agent is preferably buffered with a suitable buffering agent, such as ammonium acetate, to a pH within the range of from about 6 to about 8.

An aqueous oxidizing solution is preferred. The method, however, is suitable for the synthesis of hydrophobic peptides by the use of suitable mixtures of water miscible organic solvents and water. A preferred organic solvent is methanol which can be used at a level of up to about 75 percent methanol and 25 percent water.

The acidic peptide solution is then added incrementally to the solution of oxidizing agent at a rate of from about 1 to about 200 ml of peptide solution per hour. The pH of the reaction mixture of the increment of peptide solution and solution of oxidizing agent is constantly monitored and is maintained within the range of from about 6 to about 8, preferably 6.5 to 7.5, during the addition of the peptide solution by the addition of a suitable base, such as ammonium hydroxide. The reaction mixture is constantly agitated during addition and reaction of the peptide solution. The temperature of the reaction is not critical and can be in the range of from about 0° C. to about 50 ° C. Air is preferably avoided and can be eliminated by use of a slow flow of Nitrogen or other inert gas over the surface of the reaction mixture.

After the addition of the last increment of the peptide solution, the reaction mixture is continually agitated until no free sulfhydryl groups are detected by the Habeeb method (A.S.S.A. Habeeb, Methods Enzyol. V25, p 457, (1972) using Ellman's eagent. (G Ellman Arch, Biochem. Biophys v82, p 70, (1959). This is usually a period of from about 1 to about 3 hours. Thereafter, the reaction mixture is acidified to a pH of less than about 5 and is filtered. The peptide is recovered from the reaction mixture by any suitable technique, such as ion exchange chromatography.

The following example further illustrates various features of the present invention, but is intended to in no way limit the scope of the invention which is defined in the appended claims.

EXAMPLE 2

The linear form of somatostatin prepared in accordance with EXAMPLE 1 is treated by the method of the present invention to provide a cyclic somatostatin peptide. Four grams of the linear somatostatin are dissolved in 2.500 ml of five percent acetic acid having a pH of 3. Two and a half grams of potassium ferricyanide is dissolved in one and a half liter of water containing five grams of ammonium acetate and having a pH of 6.9. The somatostatin peptide solution is added dropwise to the ferricyanide solution at a rate of 140 ml per hour. The reaction mixture is constantly stirred during the addition of the peptide solution under Nitrogen.

A pH stat is used to monitor the pH of the reaction mixture and the pH is maintained in the range of 6.8–7 throughout the reaction by the addition of a 10 percent ammonium hydroxide solution, as required. After addition of the last increment of the peptide solution, the reaction is continued for 2 hours under conditions of constant stirring.

The pH is then reduced to 5 with acetic acid and the yellowish, greenish slightly turbid solution is filtered over celite. The filtered solution is then applied onto and filtered through a weakly basic anion exchange resin (Bio Rad AG AG3×4A column, 100–200 mesh, chloride form—300 ml) under mild suction. All of the ferro and ferricyanide anion is removed in this step. The clear solution (4–5 liters, including the different washes used in the celite filtration and the anion exchange transfer) is applied onto a weakly acidic carboxylic cation exchange resin (Bio Rex 70 column, 200 ml—acidic form) which runs overnight. The following morning 90 percent of the peptide has been retained on the cation exchange column. The retained peptide is washed with 200 ml of 5 percent acetic acid. The peptide is then eluted from the cation exchange column by washing the column with 500 ml of 50 percent acetic acid. The peptide containing fractions (about 200 ml) are concentrated on a rotary evaporator to a volume of 30 ml. The peptide is then lyophilized after dilution with water to 300 ml to provide a yield of 2.100 grams/15 grams peptide resin. The crude off-white colored material is found to be 60 percent pure by high pressure liquid chromatography.

A similar peptide prepared by use of the duVigneaud method produces a compound which is less than 30% pure, i.e. containing large amounts of polymeric material. The method of the present invention is significantly better since it not only provides better yields, but also permits use of much purer crude materials. The method of the invention is easier and requires less involved and less expensive purification procedures.

What is claimed is:

1. A method for forming a disulfide bridge in peptides containing at least one pair of cysteine moieties comprising preparing a solution of a peptide containing at least one pair of cysteine moieties, preparing a solution of an oxidizing agent, adding said peptide solution in increments to said solution of oxidizing agent, monitoring the pH of the reaction mixture comprising the solution of oxidizing agent and the increment of the peptide solution and maintaining the pH of the reaction mixture at a level of from about 6 to about 8, the period between addition and the size of said increments being such that the oxidizing reaction to form the disulfide bond occurs substantially instantaneously and the sulfhydryl concentration during the reaction remains substantially constant and at a level of substantially zero.

2. A method in accordance with claim 1, wherein the pH of the peptide solution is maintained at a level of less than about 5 prior to addition of the peptide solution to the solution of oxidizing agent.

3. A method in accordance with claim 1, wherein said pH is monitored at a level of from about 6.5 to about 7.5.

4. A method in accordance with claim 1, wherein said oxidizing agent is a ferricyanide salt.

5. A method in accordance with claim 1, wherein said peptide is selected from the group consisting of somatostatin and analogs of somatostatin.

6. A method in accordance with claim 1, wherein said peptide is selected from vasopressin and analogs of vasopressin.

7. A method in accordance with claim 1, wherein said peptide is selected from the group consisting of oxytocin and analogs of oxytocin.

8. A method in accordance with claim 1, wherein said peptide is selected from the group consisting of calcitonins and analogs of calcitonins.

9. A method in accordance with claim 1, wherein the sulfhydryl group of said cysteine moieties is generated in situ.

10. A method in accordance with claim 9, wherein said sulfhydryl groups of said cysteine moieties are protected in the form of the silver salt and said oxidizing solution contains chloride ions to deprotect said sulfhydryl groups and generate sulfhydryl groups in situ.

11. A method in accordance with claim 9, wherein said sulfhydryl groups of said cysteine moieties are protected in the form of the mercury salt and said oxidizing solution contains sulfide ions to deprotect said sulfhydryl groups and form said sulfhydryl groups in situ.

12. A method in accordance with claim 1, wherein said oxidizing solution contains methanol.

* * * * *

UNITED STATES PATENT AND TRADEMARK OFFICE
CERTIFICATE OF CORRECTION

PATENT NO. : 4,216,141

DATED : August 5, 1980

INVENTOR(S) : Jean E. F. Rivier et al.

It is certified that error appears in the above—identified patent and that said Letters Patent is hereby corrected as shown below:

Column 2, line 38, "moeities" should read -- moieties --.

Column 5, line 44, Step 14, "31" should read -- 3 --.

Column 6, line 60, "eagent" should read -- reagent --.

Signed and Sealed this

Eleventh Day of August 1981

[SEAL]

Attest:

Attesting Officer

GERALD J. MOSSINGHOFF

Commissioner of Patents and Trademarks